United States Patent
Policello et al.

(10) Patent No.: US 6,890,886 B2
(45) Date of Patent: May 10, 2005

(54) AGRICULTURAL COMPOSITIONS EMPLOYING ORGANOSILOXANES CONTAINING POLYHYDRIC GROUPS

(75) Inventors: George A. Policello, Ossining, NY (US); Gerald J. Murphy, Hopewell Junction, NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/858,708

(22) Filed: May 16, 2001

(65) Prior Publication Data

US 2002/0082170 A1 Jun. 27, 2002

Related U.S. Application Data

(60) Provisional application No. 60/204,842, filed on May 17, 2000.

(51) Int. Cl.[7] .............................. A01N 3/02; A01N 57/00
(52) U.S. Cl. .................... 504/116.1; 504/206; 504/360; 504/632
(58) Field of Search .................................. 504/360, 362, 504/206, 116.1, 358, 116; 514/770

(56) References Cited

U.S. PATENT DOCUMENTS

| | | | |
|---|---|---|---|
| 3,389,160 A | | 6/1968 | Reid |
| 4,481,365 A | * | 11/1984 | Forster et al. ............... 556/422 |
| 5,508,249 A | * | 4/1996 | Narayanan et al. ......... 504/116 |
| 5,891,977 A | | 4/1999 | Dietz et al. |
| 5,998,331 A | * | 12/1999 | Policello ..................... 504/116 |
| 6,001,140 A | | 12/1999 | Grabowski et al. |

FOREIGN PATENT DOCUMENTS

| EP | 0 535 596 | 4/1993 |
|---|---|---|

\* cited by examiner

*Primary Examiner*—Alton Pryor

(57) ABSTRACT

The present invention teaches polyhydric organosilicones and their use, a preferred of which is as adjuvants for pesticides. The polyhydric organosilicone have siloxane backbones with pendant, terminal or intermediate polyhydric groups. The polyhydric groups or the silioxane may be functionalized further with amine, alkyl and/or alkyleneoxide groups.

23 Claims, No Drawings

AGRICULTURAL COMPOSITIONS EMPLOYING ORGANOSILOXANES CONTAINING POLYHYDRIC GROUPS

CROSS REFERENCE TO RELATED APPLICATION

This application claims priority from U.S. Provisional Application Ser. No. 60/204,842, filed on May 17, 2000.

BACKGROUND OF THE INVENTION

Many herbicides require the addition of an adjuvant to the spray mixture to provide wetting and spending on foliar surfaces. Often that adjuvant is a surfactant, which can perform a variety of functions, such as increasing spray droplet retention on difficult to wet leaf surfaces, or to provide penetration of the herbicide into the plant cuticle. These adjuvants are provided either as a tankside additive or used as a component in herbicide formulations.

Sandbrink, et al., Pest. Sci. 1993, 38, 272–273, published that a TSE antagonized glyphosate performance relative to glyphosate alone in the control of Panicum maximum Jacq. Snow, et al., Langmuir, 1993, 9, 424–30, discusses the physical properties and synthesis of novel cationic siloxane surfactants. These siloxanes are based on the reaction of a chloropropyl modified trisiloxane with an alkanolamine, such as N-methyl-ethanolamine, which was further reacted with a halide to make a quaternary surfacatant.

Petroff, et al., EP 92116658, describes cationic, quaternary trisiloxanes to enhance the efficacy of glyphosate on velvetleaf, a broadleaf weed.

Henning, et al., DE 4318537, describes cationic siloxanyl modified polyhydroxy hydrocarbon or carbohydrate for use with plant protection agents. These compounds are derived from a saccharide containing 1 to 10 pentose and/or hexose units, modified with a quaternary ammonium group, and a siloxane moiety.

Reid, et al., U.S. Pat. No. 3,389,160, describes amino modified siloxane alkoxylates where the amino functionality appears as the terminal group on the alkyleneoxide moiety, opposite the siloxane group.

Policello, U.S. Pat. No. 5,998,331, discloses amino modified siloxanes wherein the amine is bound by an ether bound to the siloxane backbone wherein the amine may be terminal or pendant to the backbone and may be substituted with one or two hydroxyalkyl groups.

Dietz et al., in U.S. Pat. No. 5,891,977 describes organopolysiloxanes comprising polyhydroxyorganyl radicals and polyalkylene radicals, their process and use.

Specifically these materials are described as being useful in coatings, paints and inks, as well as emulsifiers for water-in-oil and oil-in-water systems, such as hair care formulations. Although these materials are mentioned as being practical for many applications, these were not shown to have utility as adjuvants for agrochemical applications.

In U.S. Pat. No. 6,001,140 and in copending application Ser. No. 09/211,909, siloxane polymers having polyhydric groups, such as hydrosilation products of trimethylpropane monoallyl ether, ethoxylated pentaerythritol allyl ether, propoxylated pentaerythritol allyl ether, tri-isopropanolamine allyl ether, ethoxylated allyl sorbitol, 1,3-allyloxypropanediol and 2-butyne-1,4-diol are described as useful diesel fuel additives.

SUMMARY OF THE INVENTION

The present invention teaches certain compositions comprising an organosiloxane copolymer in argricultural formulations. The organosiloxane copolymers used in the present invention are characterized as containing an average of at least one polyhydric group having at least three hydroxyls, such as a sugar group, or at least one polyhydric group having at least two hydroxyls and at least one other group which comprises a polyether, attached to the organosiloxane via a bridging group.

The copolymers described above, are useful as adjuvants and additives for applications with pesticides, such as, but not limited to, herbicides, insecticides, fungicides and growth regulators, as well as fertilizers and micronutrients.

Optionally, the polyhydric organosiloxanes used in this invention may be blended with conventional trisiloxane alkoxylates (TSAs). Blends of these polyhydric organosiloxanes with TSAs provide enhanced wetting properties on difficult to wet plant surfaces.

Additionally the polyhydric organosiloxanes of this invention may be blended with conventional organic surfactants, as emulsifers, dispersants, coadjuvants or cosurfactants.

In various aspects, the invention embodies compositions of polyhydric organosiloxanes, treatment methods, and novel organosiloxane structures.

DETAILED DESCRIPTION OF THE INVENTION

The polyhydric organosiloxanes are useful as adjuvants for herbicide applications.

Polyhydric Organosiloxanes

As used herein, the term "polyhydric organic group" refers to an organic group having two or more hydroxyl groups thereon. Preferred organic groups are saturated ether or saturated hydrocarbon groups. Polyhydric unsaturated aliphatic groups may be employed but are generally less preferred. The term "polyhydric organosiloxane" refers to compounds with at least one Si—O—Si bond, which have at least one polyhydric group attached to silicon through a bridging group by a Si—C bond.

Polyhydric organosiloxanes useful in the inventive compositions may include such copolymers as described in U.S. Pat. No. 5,891,977, U.S. Pat. No. 6,001,140 and in commonly owned copending application Ser. No. 09/211,909, all incorporated herein by reference. Preferred polymers have no more than 20 siloxane repeat units and/or also have polyether (i.e. polyalkylene oxide) substituents. The polyether substituents may be present as separate groups, or as part of the polyhydric group structure. In the case where the polyhydric group contains only two hydroxyl groups thereon, the polyhydric organisiloxanes used in the invention comprise at least one other group which includes polyether structure.

The polyhydric organic groups may be aliphatic, low molecular weight hydrocarbon groups, optionally interrupted with one or more ether oxygen atoms, and having at least two hydroxy groups thereon. The polyhydric group preferably is saturated completely, as disclosed in U.S. Pat. No. 6,001,140, although unsaturated polyhydric groups such as disclosed in DE 4,032,006 may also be employed.

The polyhydric group is preferably derived from a mono-, di-, oligo- or polysaccharide, or its glycosides or a corresponding derivative thereof. Examples of polysaccharides which may be utilized to form polyhydric groups, are glucose, maltose, raffinose, sorbitol, glucosamine, glucopyranosylamine, glucamine, N-methylglucamine, isomaltamine, gluconic acid, and heptagluconic acid.

When the siloxane copolymer is not a trisiloxane, it is preferably further characterized by having an average at least one polyalkyleneoxide ("polyether" group). In the case of a trisiloxane a polyalkyleneoxide group may optionally be present on the copolymer used in the invention. The polyalkyleneoxide groups may be provided in the bridging group which links the polyhydric group to a silicon atom of the organosiloxane, it may be provided as a separate group attached to a silicon atom of the organosiloxane, or both. As a further option, the organosiloxane copolymer may contain an amino group, either as separate substituent group or as part of the polyhydric group-containing substituent or a polyether group-containing substituent.

In a particular embodiment the polyhydric organosiloxanes of the present invention have the average general formula:

$$[SiO_{4/2}]_f[MeSiO_{3/2}]_d[O_{1/2}MeSi(Q)O_{1/2}]_e[O_{1/2}SiMe_2Q]_g \qquad (I)$$

wherein f is 0 to 50, preferably 1 to 5, more preferably 1 to 2, most preferably 1; d=0 to 2, preferably 0, e=0 to 3, most preferably 0, g is, if the siloxane is not cyclic, 2+e+2d, or zero if the siloxane is cyclic;
the Q groups are independently $R^1$ or $$-B(O)_j(C_aH_{2a}O)_bR(L)_tV \qquad (II)$$

wherein

B is a divalent bridging group of $C_1$ to $C_6$, preferably $C_3$ to $C_4$, j=0 or 1, preferably 1, each a is 2 to 4, preferably 2 to 3, each b is 0 to 15, preferably 0 to 8, R is a divalent organic group containing 2 to 8 carbons, preferably 3 to 4 carbons, each optionally OH substituted, L is $NR^2$, where $R^2$ may be hydrogen, an amino alkyl of one to four carbons, or an alkyl of 2 to 4 carbon atoms which may have hydroxy substitutions thereon, or $R^1$, t=0 or 1, preferably 0, and V is a polyhydric radical containing a number, n, of groups (C—OH), where n is $\geq 2$, preferably from 2 to 30, most preferably from 5 to 15; $R^1$ is either a polyether of the general structure $B(O)_j(C_aH_{2a}O)_bR^3$ or an alkyl radical containing 1 to 18 carbons, preferably methyl, $R^3$ is hydrogen, a hydrocarbon group of 1 to 4 carbons or $N(R^2)_2$, preferably hydrogen;
At least one Q is not $R^1$; and
When n is 2 at least one $R^1$ group is present of said polyether general structure.

Preferably most $R^1$ groups are methyl, but some may be polyethers of the structure $-C_aH_{2a}O)_bR^3$ as defined above. Exemplary B are —(CH$_2$)$_2$—, —(CH$_2$)$_3$—, and —CH$_2$CH(OH)CH$_2$—. Exemplary R groups are —(CH$_2$)$_2$—, —CH$_2$CH(OH)CH$_2$—, —(CH$_2$)$_3$, and —CH$_2$C$_6$H$_{11}$(OH)CH$_2$—. Examples of $R^2$ are —CH$_3$, —C$_2$H$_5$, —C$_2$H$_4$OH, (C$_2$H$_4$O)$_3$(C$_3$H$_6$O)$_2$H; —(C$_2$H$_4$O) CH$_3$; and —(C$_3$H$_6$O)$_3$OH.

The polyhydric group V is preferably a group formed from a mono-, di-, oligo- or polysaccharide, or its glycosides or corresponding derivatives. Examples thereof are derived from glucose, maltose, raffinose, sorbitol, glucosamine, glucopyranosylamine, glucamine, N-methyglucamine, isomaltamine, gluconic acid, and heptagluconic acid, and alkoxylates thereof. Other V groups may be derived from trimethylolpropane, pentaerythritol, tri-isopropanolamine, and 2-butyne-1,4-diol.

Preferred Q structures are wherein B is propylene, j=1, a=2, b=0 to 4, R=—CH$_2$CH(OH)CH$_2$—, t is 0 and V is N(CH$_3$)CH$_2$[CH(OH)]$_4$CH$_2$OH (a radical obtained from N-methylglucamine). Specific Q groups of formula (II) are:

—C$_3$H$_6$OCH$_2$CH(OH)CH$_2$N(CH$_3$)CH$_2$[CH(OH)]$_4$CH$_2$OH;
—C$_3$H$_6$O[C$_2$H$_4$O]$_4$CH$_2$CH(OH)CH$_2$N(CH$_3$)CH$_2$[CH(OH)]$_4$CH$_2$OH; and
—C$_3$H$_6$O[C$_2$H$_4$O]$_4$[C$_3$H$_6$O]$_2$CH$_2$CH(OH)CH$_2$N(CH$_3$)CH$_2$[CH(OH)]$_4$CH$_2$OH.

In an alternative embodiment, some or all of the methyl groups in formula (1) above may be replaced by other alkyl groups, for instance ethyl, isopropyl, n-propyl or butyl groups, or by phenyl groups.

Particularly preferred compounds are methyl terminated trisiloxanes, that is compounds of formula (1) in which f=1, d=0, e=0, g=2, the terminal Q groups are methyl and the pendant Q group is a group of formula (II).

Other Siloxanmes

In addition to the polyhydric polyorganosiloxanes employed in the invention, the compositions of the present invention optionally may include TSAs of the general formula:

$$R_4Me_2SiO[MeSi(G)O]_xSiMe_2R^4$$

Wherein x=0 to 2, preferably 1, G=C$_m$H$_{2m}$O(C$_2$H$_4$O)$_y$(C$_3$H$_6$O)$_w$R$^5$, m=2 to 4, preferably 3, y=3 to 20, preferably 4 to 8, w=0 to 8, providing that when w is >0, (y+w) is preferably between 5 and 12. $R^5$ is hydrogen, acetyl or a hydrocarbon radical between 1 and 4 carbon atoms. $R^4$ is G, or an alkyl of one to four carbons. The preferred nonionic siloxane alkoxylates are trisiloxane alkoxylates, where x=1, m=3, y=4to8, w=0, $R^4$ is Me and $R^5$ is H or Me.

Still further, compositions of the invention may include polyorganosiloxanes having both polyether and amino functionality, such as described in U.S. Pat. No. 5,998,331, incorporated herein by reference.

Pesticides

The compositions of the present invention also optionally include pesticides, especially acid functionalized ones, i.e., compounds that contain at least one carboxylic, sulfonic or phosphonic acid group or their salt or ester. The term pesticide means any compound used to destroy pests, e.g., rodenticides, fungicides, and herbicides. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxapropethyl, fluazifop-p-butyl, haloxyfop-methyl, quizalofop, sethoxydim, dichlobenil, isoxaben, and bipyridylium compounds.

Excipients

The composition also may include fatty acid esthers, e.g., methyl soyate, for crop oil concentrate formulations, as well as water, for aqueous applications. Buffers, preservatives and other standard excipients known in the art also may be included in the composition. When the compositions of the present invention are insoluble in distilled water, spreading may be achieved by the addition of a small amount of an acid, such as acetic acid, to protonate the amine functionality, thereby increasing water solubility. Moreover, other cosurfactants which do not interfere with superspreading, may be included, for instance cosurfactants which have short chain hydrophobes ($C_{10}$ or less, not counting any branching carbons) or alkyleneoxide copolymers such as sold under the trademarks PLURONIC® and TETRONIC® (both BASF Corp.) and UNCON® (Union Carbide/Dow Corp). Examples of such cosurfactants and their use can be found in U.S. Pat. No. 5,104,647, U.S. Pat. No. 5,558,806 and EP 0862857, all incorporated herein by reference.

Manufacture

The polyhydric organosiloxanes used in the present invention may be made by the hydrosilation of a hydridosiloxane with an epoxy intermediate, such as allyl glycidyl ether, vinyl cyclohexene monoxide, or an epoxy terminated allyl polyalkyleneoxide, followed by ring opening the epoxide with the appropriate amino group. The hydridosiloxanes described are commercially available and may be made as known in the art. Hydrosilation are within the general conditions taught in Marciniec, *Comprehensive Handbook of Hydrosilylation*, edited by Bogdan Marciniec, Pergamon Press.

Alternatively an epoxy terminated allyl polyalkyleneoxide may be hydrosilated onto a hydridosiloxane backbone and then the epoxide is ring opened with the desired amine. Epoxy terminated, allyl polyethyleneoxide can be prepared by the method outlined by Xue-Ping Gu, et al., (Synthesis of Glycol Diglycidyl Ethers Using Phase Transfer Catalysis; in *Synthesis Communications* June/July 1985, p.649–651) from an epoxide and commercially available allyl started polyalkylene oxides.

Alternatively one may start from the reaction product of an allyl or methallyl chloride and a polyhydric amine compound and hydrosilate this allylic polyhydric amine onto hydridosiloxanes.

Still an alternate approach is to start with an alkoxylated allyl or methall ylamine and hydrosilate this onto hydridosiloxanes. Hydrosilation conditions depend on the amine and siloxane, but are within the general conditions taught in Marciniec.

Additionally, one may employ a hydrosilation reaction of a hydridosiloxane and an aliphatically unsaturated polyhydric species, preferably an olefinically unsaturated polyhydric species. Exemplary olefinically unsaturated polyhydric species include allyl glucose, sorbitol monoallylether, allylpolyalkylenoxides terminated with a polyhydric group, and monoallylethers of an alkoxylated polyhydric group, such as the monoallylether of alkoxylated sorbitol or glucose. Trimethylolpropane monoallyl ether (TMPMAE), alkoxylated trimethylolpropane monoallyl ether, pentaerythritol allyl ether, alkoxylated pentaerythritol allyl ether, triisopropanolamine monoallyl ether and 2-butyne-1,4-diol are further examples of compounds which may be hydrosilated in this manner to form a polyhydric polyorganosiloxane. Alkoxylation may be ethoxylate, propoxylate, butoxylate or mixtures thereof and may contain multiple alkoxylate units per molecule, preferably from 1–6 such repeat units.

The polyhydric compound may be commercially available, e.g., N-Methylglucamine, but polyalkylene oxide modified or substituted versions thereof may be manufactured as known in the art.

Polyhydric organosiloxanes having both polyether and polyhydric species on the same molecule may be provided by sequential or simultaneous hydrosilations of allyl started polyethers and allyl finctional polyhydric compounds using hydridosiloxanes having greater than one hydrido groups per molecule.

Use

The polyhydric organosiloxanes may be used in agricultural applications as adjuvants for pesticides, wherein the siloxane is applied in a pesticide formulation to argricultural products. The composition of the present invention is useful as a tank side additive, or as a component in a herbicide formulation. In addition the compositions of the present invention are useful as adjuvants for other pesticides, such as, fungicides, insecticides, plant growth regulators, acaracides and the like. The pesticide formulations may be wet, dry, slurries or other formulations as are known in the art.

The siloxanes are added directly to a spray tank along with an acid functional pesticide, or as part of a pesticide formulation. When used as a tankside additive, the siloxane is present at weight concentrations between 0.001% and 5.0% preferably between 0.025% and 0.5%. Likewise, when the polyhydric organosiloxanes are used in a pesticide formulation (in-can), they are present at weight concentrations that will deliver between 0.001% and 5.0% to the final use dilution, preferably between 0.025% and 0.5%, of the final use dilution.

It is noted that most dilutions will be made with water, but in the case of crop oil concentrates, oils (mineral, silicone, animal or vegetable oils) will be the diluents.

When the compositions of the present invention are used in conjunction with a TSA, the weight ratio of the TSA to the polyhydric organosiloxanes is between 5:95 and 95:5, preferably between 5:95 and 40:60. The blend may be accomplished by mixing physically the two components prior to use, or by adding them separately to a spray mixture at the point of use.

When the compositions of the present invention are used in conjunction with nonsilicone surfactants, the weight ratio of the nonsilicone surfactant to the polyhydric organosiloxane is between 1:99 and 99:1, preferably between 99:1 and 40:60.

The polyhydric organosiloxanes also may be used generally as surface active agents in aqueous formulation where there is an acid functionalized component. The polyhydric organosiloxanes also may be used as surface active agents, including, but not limited to, as surfactants, wetting agents and softeners for textiles, flow and leveling agents in coatings, hair care products, skin care and creams for personal care applications and anti-static agents, detergents and softeners for laundry products.

EXAMPLES

Unless otherwise indicated, all parts and percentages are by weight, and are based on the weight at the particular stage of the processing being described.

Example 1 a. Invention Polyhydric Silicone Surfactant

The polyhydric organosiloxane was prepared by the slow addition of the desired polyhydric amino compound to a reaction vessel containing heptamethyltrisiloxane modified with allyl glycidyl ether, using 2-propanol (30 wt %) as a solvent. The epoxy siloxane intermediate was

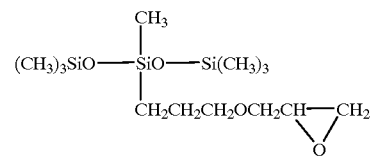

Therefore, 50.0 g (0.149 moles) of a trisiloxane, epoxy intermediate, 37.8 g (0.194 moles) of N-methylglucamine along with 37.6 g 2-propanol were combined in a round-bottom flask equipped with a reflux condenser and an overhead stirrer. The reaction mixture was catalyzed with 0.2 g titanium (IV) butoxide and the flask temperature was slowly to reach a maximum of 83° C. The flask contents were held at this temperature until the epoxy content, as determined by a perchloric acid titration, on a sample of the reaction mixture, showed that the epoxide content was nil, indicating the reaction was complete (~23 h). A small amount of water along with 15 g of isopropanol was added to the reaction mixture and stirred for 1 hour. The addition of the water deactivated the titanium catalyst. The mixture was filtered through a medium filter pad and stripped on a rotary evaporator for 1.5 hours at 70° C. and 1.0 mm Hg to afford the desired product, which had an aqueous surface tension of 20 mN/m (0.1 wt %, 25° C.).

An example of a polyhydric organosiloxane is described in Table 1. Other compositions of polyhydric organosiloxanes may be prepared according to this procedure.

TABLE 1

Description of Polyhydric Organosiloxanes

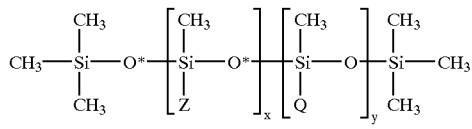

| Reference | x | y | Description |
|---|---|---|---|
| SIL-1 | 0 | 1 | Q = $C_3H_6OCH_2CH(OH)CH_2-N(CH_3)CH_2[CH(OH)]_4CH_2OH$ | b. Comparative Silicone Based Surfactant $Me_3SiO[MeSi(C_3H_6O(C_2H_4O)_8H)O]_1SiMe_3$ (SIL-A) is a comparative TSA. This material was prepared by standard hydrosilation of an allyl terminated polyether with heptamethyltrisiloxane.

c. Comparative Nonsilicone Surfactants

Table 2 provides descriptions of typical, comparative, nonsilicone surfactants.

TABLE 2

Description of Comparative Conventional Nonsilicone Surfactants

| Reference | Moles EO | Remarks |
|---|---|---|
| OPE | 10 | Octylphenol ethoxylate (TRITON ® X-100) (Union Carbide Corp., Danbury, CT) |
| TAE | 15 | Tallow amine ethoxylate (ETHOMEEN ® T/25) (Akzo Nobel Chemicals Inc.; Chicago, IL) |

Example 2

This example demonstrates the utility of the polyhydric organosilicone used in this present invention as surfactants. Surface tension was measured using a Cahn microbalance, with a sand blasted platinum blade as the sensor. Solutions of the various components were prepared at 0.1 wt % in 0.005M NaCl water (Deionized), as an equilibrium aid. Aqueous solutions of these unique compositions provide a significant reduction in surface tension relative to conventional surfactants. Additionally the polyhydric moiety does not detract from the surface tension lowering associated with traditional TSA (SIL-A), see Table 4.

The compositions of the present invention also provide enhanced spreading similar to the TSAs (SIL-A), and relative to conventional surfactants (OPE and TAE), see Table 4.

Spreading was determined by applying a 10 µL droplet of surfactant solution to a polyester film (3M, IR 1140 transparency film) and measuring the spread diameter after 30 seconds. The solution was applied with an automatic pipette to provide droplets of reproducible volume. Deionized water that was further purified with a Millipore filtration system was used to prepare the surfactant solutions.

The spreading properties of the polyhydric organosiloxane SIL-1 are equal to those of trisiloxane ethoxylates such as SIL-A, demonstrating that the siloxane having a polyhydric moiety was an effective spread enhancer.

TABLE 4

Comparison of Aqueous Surface Tension Properties

| | | Spread Diameter (mm) | |
|---|---|---|---|
| Surfactant | Surface Tension (mN/m) | 0.1 wt% | 0.2 wt% |
| SIL-1 | 20 | 45 | 48 |
| SIL-A | 21 | 44 | 42 |
| OPE | 29 | nd | 8 |
| TAE | 41 | nd | 6 |
| None[b] | 72 | * | — |

[a]Surface tension in mN/m at 25° C.
[b]Surface tension of water from CRC Handbook of Chemistry and Physics; 63 Edition, 1982–1983.
*Spread diameter of distilled water = 4 mm The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto. Further, the specific features recited in the respective dependant claims can be combined in any other manner with the features of the independent claims and any of the other dependent claims, and all such combinations are expressly contemplated to be within the scope of the invention.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

What is claimed is:

1. A composition consisting essentially of:
   a) at least one polyhydric organosiloxane having the average formula:

$$(SiO_{4/2})_d(MeSiO_{3/2})_e(O_{1/2}MeSi;(Q)O_{1/2})_f(O_{1/2}MeSi_2Q)_g \quad (I)$$

wherein
   f is 0 to 50, d=0 to 2, e=0 to 3, g is, if the siloxane is not cyclic, 2+e+2d, or zero if the siloxane is cyclic, with the proviso that f, d, e, and g are not all 0;
   the Q groups are independently $R^1$ or $$-B(O)_j(C_aH_{2a})_bR(L)_tV \quad (II)$$

wherein B is a divalent bridging group of $C_1$ to $C_6$, j=0 or 1, each a is 2 to 4, each b is 0 to 15, R is a divalent organic group containing 2 to 8 carbons which may be optionally OH substituted, L is $NR^2$, $R^2$ is hydrogen, an amino alkyl of one to four carbons, an alkyl of 2 to 4 carbon atoms which may have hydroxy substitutions thereon, or $R^1$, t=0 or 1, and V is a polyhydric radical containing a number, n, of groups (C—OH), where n is $\geq 2$;
   $R^1$ is either a polyether of the general structure $B(O)_j(C_aH_{2a})_bR^3$ or an alkyl radical containing 1 to 18 carbons,
   $R^3$ is hydrogen, a hydrocarbon group of 1 to 4 carbons or $N(R^2)_2$;
   at least one Q is not $R^1$; and
   when n is 2 at least one $R^1$ group is present in said polyether general structure;
   b) a pesticide selected from the group consisting of a growth regulator, a photosynthesis inhibitor, a pigment inhibitor, a mitotic disrupter, a lipid biosynthesis inhibitor, a cell wall inhibitor, a cell membrane disrupter, a phenoxy acetic acid, a phenoxy propionic acid, a phenoxy butyric acid, a benzoic acid, a triazine, a substituted urea, bentazon, desmedipham, methazole, phenmedipham, pyridate, amitrole, clomazone, fluridone, norflurazone, dinitroaniline, isopropalin, oryzalin, pendimethalin, prodiamine, trifluralin, glyphosate, sulfornylurea, imidazolinone, clethodim, diclofop-methyl, fenoxaprop-etthyl, fenoxaprop-ethyl, fluazifop-p-butyl, haloxyfop-methyl, quizalofop, sethoxydim, dichiobenil, isoxaben, a bipyridylium and an uracil;
   c) optionally a trisiloxane alkoxylate of the formula:

$$R^4Me_2SiO(MeSi(G)O)_xSiMe_2R^4$$

Wherein x=0 to 2, $G=C_mH_{2m}O(C_2H_4O)(C_3H_6O)_wR^5$, m=2 m=to 4, y=3 to 20, w=0 to 8, $R^5$ is hydrogen, acetyl or a hydrocarbon radical having between 1 and 4 carbon atoms, and $R^4$ is G, or an alkyl of one to four carbon atoms; and d) and optionally an organic nonionic, anionic, or cationic surfactant.

2. A composition as in claim 1 wherein the polyhydric organosiloxane a) has at least one polyether group thereon.

3. A composition as in claim 1 wherein the polyhydric organosiloxane a) has at least one amino group thereon.

4. A composition as in claim 1 wherein the polyhydric organosiloxane is an organosiloxane comprising a group formed from a mono-, di-, oligo- or polysaccharide, or a glycoside thereof.

5. A composition as in claim 1 wherein f is 1–5, d is 0, e is 0, and g is 2.

6. A composition as in claim 1 wherein at least one Q is $R^1$ and at least one $R^1$ is $-(C_aH_{2a}O)_bR^3$.

7. A composition as in claim 1 wherein, in formula (II), B is propylene, j=1, a=2, B=0 to 4, R is $-CH_2CH(OH)CH_2-$ and t is 0.

8. A composition as in claim 1 wherein the group of formula (II) is
   $-C_3H_6OCH_2CH(OH)CH_2N(CH_3)CH_2(CH(OH))_4CH_2OH$;
   $-C_3H_6O(C_2H_4O)_4CH_2CH(OH)CH_2N(CH_3)CH_2(CH(OH))_4CH_2OH$; or
   $-C_3H_6O(C_2H_4O)_4(C_3H_6O)_2CH_2CH(OH)CH_2N(CH_3)CH_2CH(OH)_4CH_2OH$.

9. A composition as in claim 1 wherein the group V is derived from glucose, maltose, raffinose, sorbitol, glucosamine, glycopyranosylamine, glucamine, N-methylglucamine, isomaltamine, gluconic acid, heptagluconic acid, timethylolpropane, pentaerythritol, triisopropanolamine or 2-butyne-1, 4-diol.

10. A composition as in claim 1 wherein the pesticide is an acid functional pesticide.

11. A composition as in claim 1 wherein the trisiloxane alkoxylate of the formula:

$$R^4Me_2SiO(MeSi(G)O)_xSiMe_2R^4$$

wherein x=0 to 2, $G=C_mH_{2m}O(C_2H_4O)_y(C_3H_6O)_wR^5$, m=2 to 4, y=3 to 20, w=0 to 8, $R^5$ hydrogen, acetyl or a hydrocarbon radical having between 1 and 4 carbon atoms, and $R^4$ is G, or an alkyl of one to four carbon atoms is present.

12. A composition as in claim 11 wherein the weight basis ratio of the trisioxane alkoxylate c) to the polyhydric organosiloxane a) is between 5:95 and 95:5.

13. A composition as in claim 1 wherein the organic nonionic, anionic or cationic surfactant is present.

14. A composition as in claim 1 wherein water.

15. A composition as in claim 14 wherein the polyhydric organosiloxane a) is present at a concentration of from 0.001% to 5.0%.

16. A composition as in claim 1 wherein the weight basis ratio of the polyhydric organosiloxane a) to the pesticide b) is from 1:99 to 99:1.

17. A composition as in claim 1, wherein the pesticide is selected from the group consisting of a growth regulator, a photosynthesis inhibitor, a pigment inhibitor, a mitotic disrupter, a lipid biosynthesis inhibitor, a cell wall inhibitor, and a cell membrane disrupter.

18. A composition as in claim 1, wherein the pesticide is selected from the group consisting of a phenoxy acetic acid, a phenoxy propionic acid, a phenoxy butyric acid, a benzoic acid, a triazine, a substituted urea, bentazon, desmedipham, methazole, phenmedipham, pyridate, amitrole, clomazone, fluridone, norflurazone, dinitroaniline, isopropalin, oryzalin, pendimethalin, prodiamine, trifluralin, glyphosate, sulfornylurea, imidazolinone, clethodim, diclofop-methyl, fenoxaprop-etthyl, fenoxaprop-ethyl, fluazifop-p-butyl, haloxyfop-methylquizalofop, sethoxydim, dichlobenil, isoxaben, a bipyridylium and an uracil.

19. A composition as in claim 1 wherein n is from 2 to 30.

20. A composition as in claim 1 wherein n is 5 to 15.

21. A process for treating plants comprising applying to plants a composition as in claim 1.

22. A composition as in claim 1 wherein in formula (I), f=1, d=0, e=0, g=2, the terminal Q groups are methyl and the pendant Q group is a group of formula (II).

23. A composition as in claim 1 wherein a is 2 to 3, b is 0 to 8 and t is 0.

* * * * *